US007934500B2

(12) United States Patent
Madaus et al.

(10) Patent No.: US 7,934,500 B2
(45) Date of Patent: May 3, 2011

(54) METHOD AND APPARATUS FOR DETECTING THE RESPIRATORY ACTIVITY OF A PERSON

(75) Inventors: Stefan Madaus, Krailling (DE); Hartmut Schneider, Burgeln Marburg (DE); Rainer Jakobs, Munich (DE); Harald Vogele, Gauting (DE)

(73) Assignee: Map Medizin-Technologie GmbH, Martinsried (DE)

( * ) Notice: Subject to any disclaimer, the term of this patent is extended or adjusted under 35 U.S.C. 154(b) by 1111 days.

(21) Appl. No.: 11/454,835

(22) Filed: Jun. 19, 2006

(65) Prior Publication Data

US 2006/0272641 A1 Dec. 7, 2006

Related U.S. Application Data

(63) Continuation of application No. 10/070,346, filed as application No. PCT/EP01/07574 on Jul. 2, 2001, now Pat. No. 7,089,936.

(30) Foreign Application Priority Data

Jun. 30, 2000 (DE) .................................. 100 31 079

(51) Int. Cl.
*A61M 16/00* (2006.01)
*A62B 7/00* (2006.01)
*A62B 7/04* (2006.01)
*F16K 31/02* (2006.01)
*F16K 31/26* (2006.01)

(52) U.S. Cl. .......... 128/204.23; 128/204.18; 128/204.26

(58) Field of Classification Search ............. 128/204.23, 128/204.18, 204.21, 204.22, 204.26, 206.25, 128/205.25
See application file for complete search history.

(56) References Cited

U.S. PATENT DOCUMENTS

| 5,199,424 A | 4/1993 | Sullivan et al. |
| 5,245,995 A | 9/1993 | Sullivan et al. |

(Continued)

FOREIGN PATENT DOCUMENTS

DE 690 21 681 2/1996

(Continued)

OTHER PUBLICATIONS

H. Teschler et al., "Intelligent CPAP Systems: Clinical Experience," *Thorax*, 1998, vol. 53, (Supp. 3), pp. S49-54.

*Primary Examiner* — Steven O Douglas
*Assistant Examiner* — Kristen C Matter
(74) *Attorney, Agent, or Firm* — Nixon & Vanderhye P.C.

(57) ABSTRACT

A method and a device are provided for detecting the respiratory activity of a person and for controlling the time progression of breathing gas pressure, especially in accordance with physical parameters and considering parameters indicating the momentary physiological condition of the breathing person. The device for detecting the respiratory activity of a person has at least one sensor that provides a first signal indicating the breathing gas flow, wherein at least one signal processing device is provided for processing the first signal. The signal processing device is configured in such a way that said device determines a reference-relation on the basis of the first signal detected during a first time interval. On the basis thereof, the device determines a correlation-relation between the reference-relation and the first signal. The device generates an output signal indicating the respiratory activity and/or the physiological condition of the breathing person by considering at least the correlation-relation.

24 Claims, 4 Drawing Sheets

U.S. PATENT DOCUMENTS

| | | |
|---|---|---|
| 5,335,654 A | 8/1994 | Rapoport |
| 5,438,980 A | 8/1995 | Phillips |
| 5,458,137 A | 10/1995 | Axe et al. |
| 5,483,969 A * | 1/1996 | Testerman et al. ............ 600/529 |
| 5,740,795 A | 4/1998 | Brydon |
| 6,105,575 A * | 8/2000 | Estes et al. ............... 128/204.23 |
| 6,286,508 B1 * | 9/2001 | Remmers et al. ......... 128/204.18 |
| 6,318,365 B1 | 11/2001 | Vogele et al. |
| 6,491,629 B1 | 12/2002 | Bousseljot et al. |
| 7,089,936 B2 * | 8/2006 | Madaus et al. ........... 128/204.23 |
| 2002/0185131 A1 | 12/2002 | Madaus et al. |

FOREIGN PATENT DOCUMENTS

| | | |
|---|---|---|
| DE | 195 00 529 | 8/1996 |
| DE | 692 11 814 | 1/1997 |
| DE | 197 52 094 C1 | 11/1997 |
| DE | 692 22 965 | 6/1998 |
| DE | 692 24 745 | 8/1998 |
| DE | 198 37 656 | 2/2000 |
| DE | 694 22 900 | 6/2000 |
| DE | 692 30 564 | 8/2000 |
| DE | 691 32 030 | 10/2000 |
| DE | 100 31 079 A1 | 2/2002 |
| EP | 0 612 257 B1 | 11/1992 |
| EP | 0 934 723 A1 | 11/1994 |
| EP | 1 009 463 B1 | 2/1998 |
| WO | WO 93/09834 | 5/1993 |
| WO | WO 94/23780 | 10/1994 |
| WO | WO 95/32016 | 11/1995 |
| WO | WO 97/14354 | 4/1997 |
| WO | WO 98/35715 | 8/1998 |
| WO | WO 99/24099 | 5/1999 |
| WO | WO 00/10633 | 3/2000 |
| WO | WO 00/24446 | 5/2000 |
| WO | WO 00/27457 | 5/2000 |
| WO | WO 00/66207 | 11/2000 |
| WO | WO 02/00283 A1 | 1/2002 |
| WO | WO 02/083221 A2 | 10/2002 |

* cited by examiner

METHOD AND APPARATUS FOR DETECTING THE RESPIRATORY ACTIVITY OF A PERSON

CROSS REFERENCE TO RELATED APPLICATIONS

This application is a continuation of U.S. application Ser. No. 10/070,346, filed Jun. 21, 2002 now U.S. Pat. No. 7,089,936, allowed, which claims the benefit of PCT Application Serial No. PCT/EP01/07574, filed Jul. 2, 2001, which in turn claims the benefit of German Application Serial No. DE 100 31 079.6, filed Jun. 30, 2000, each incorporated herein by reference in its entirety.

The present invention is directed to a device for the detection of the respiratory activity of a person as well as for controlling the time related course of respiratory gas pressure particularly in accordance with physical parameters and parameters indicative with respect to the actual physical condition of a respirating person. The present invention may be applied particularly in the field of sleep medicine for diagnosing and/or treating sleep related breathing disorders by positive pressure respiration (CPAP-Therapy). Further, the present invention addresses a method for controlling a respiratory gas pressure in connection with excess-pressure respiratory gas supply.

CPAP-Therapy (Continuously Positive Airways Pressure-Therapy) affords prevention of sleep related breathing disorders in a physiologically well accepted manner.

By means of respiratory gas supplied at a defined elevated pressure level above ambient pressure a pneumatic splinting of the upper airways may be achieved to effectively prevent potential obstructions in this region—or to afford sufficient Oxygen supply towards the patient in case of temporarily contraction of said upper airways. To achieve high physiological acceptability it is usually envisaged to adjust a low respiratory pressure level affording sufficient pneumatic splinting of the upper airways. However, it has become evident that aforesaid low respiratory pressure level is subject to significant variations. Experiments have been made by using so called AUTO-CPAP devices which for example automatically increase the therapy pressure upon occurrence of snoring sounds, to take these variations in required CPAP-pressure into account. Further CPAP-devices are known for detecting the time related course of the breathing gas flow and analyzing same with respect to features indicative with respect to airway obstructions. In case of such airway obstructions an increase of the therapy-pressure is temporarily administered.

Also there are known Auto-CPAP devices determining the present physiological condition of a patient by means of pressure pulses applied to the respiratory gas supplied via a breathing gas conduit wherein for example on the basis of an impedance detection the present degree of obstruction may be concluded.

From EP 0 612 257 B1 there is known a system for generation of continuously positive respiratory gas pressure, which system changes the pressure level of the gas supplied to the patient in a defined manner, and which analyses changes of the airflow profile that may go along therewith.

With respect to the pressure control concepts applied so far for automatic patient-related adjustment of the breathing gas pressure there exists a problem in that the changes of the respiratory pressure administered thereby are not universally accepted by the respective patients. Further there exists a problem in that the known auto-CPAP systems start to react on significant breathing disorders only.

It is an object of the present invention to provide a device for the detection of the respiratory activity as well as for the provision of physical parameters during administration of a respiratory gas to a patient that allows a precise determination of the physiological state of the patient.

According to the present invention this object is performed by a device for detecting breathing activity of a person comprising at least one means for supplying a first signal indicative with respect to breathing gas flow; and at least one signal processing means for processing said first signal, wherein said signal processing means being construed so as to generate a reference relation on the basis of said first signal detected over a first time period, and a correlation-relation between said reference-relation and said first signal, said signal processing means being further construed so as to generate on the basis of an observation of at least said correlation-relation an output signal which is indicative with respect to the breathing activity, in particular classifying same.

This affords in an advantageous manner an extremely exact classification of the respiratory activity of the respirating person and, based thereon, meeting the patients physiological state, a precise setting of the respiratory pressure in a convenient manner without disturbing the natural sleep behaviour. The pressure control based on the precise classification or detection of the respiratory activity provides a clearly improved acceptance of therapy and allows a far sighted adjustment of the breathing gas pressure, which may prevent occurrence of potentially occurring airway obstructions with a high likelihood.

On the basis of the determination-concept according to the present invention it might be possible in an advantageous manner to ensure that a patient-specific setting of the breathing gas pressure adjusted by a respective CPAP-device is achieved with high reliability and without particular diagnostic efforts. On the basis of the determination concept according to the present invention it is further enabled to dispense from active variation of the breathing gas pressure as it was so far necessary for the supervision of the physiological state, and to determine the physiological state of the patient without arbitrarily adjusted pressure experiments.

According to a preferred embodiment of the present invention, the length of a first time period for determining the reference relation is determined so as to extend over at least two respiration cycles. It is possible to define the generation of the reference relation via a criteria-array. This criteria-array preferably includes a plurality of entries by which it is determined how the reference relation is generated from the first and second detected signals. It is possible for example to determine certain features of the reference relation by processing said first and second signals over a period which exceeds a shorter observation period for setting other features of said reference relation.

According to a particularly preferred embodiment of the present invention there is provided at least one filter-means for filtering the first and/or second signal with respect to a predetermined frequency-range. This affords to extensive suppression of certain detection-related noise impacts.

According to a further preferred embodiment of the present invention the signal processing means includes at least one smoothing means for smoothing said reference relation by application of predetermined smoothing criteria. According to a preferred embodiment, said smoothing criteria are set adaptively. It is also possible to select preset smoothing criteria for certain respiratory states, or to adapt the smoothing criteria to the detected respiratory state.

Preferably the parameters of the filter means are adaptively adjusted. The adaptation behaviour may preferably determined by input of respective parameters.

According to a particularly preferred embodiment of the present invention at least one of the aforementioned smoothing means is construed in such a manner that same effects smoothing on the basis of statistic methods.

The generation of output signals which are indicative with respect to the respiratory activity by means of said signal processing means is carried out in accordance with a preferred embodiment of the invention on the basis of a threshold observation. For this a threshold observation means processing threshold criteria in particular zero-crossings is preferably integrated into the signal processing means. Preferably, the signal processing means further includes counter means for counting accomplishment of predetermined criteria within a set time period. The time periods are preferably variably adapted to the present respiratory state.

The detection of signals indicative with respect to the breathing gas pressure may be carried out for example by means of a pressure sensor which is integrated into a respective CPAP-device and which detects for example via a sensing tube the static pressure within a region of a breathing mask applied to a patient. The signals indicative with respect to the breathing gas flow may be determined for example via a sensing shield arrangement provided in a breathing gas supply path.

By means of the device proposed according to the invention or on the basis of the analysis procedure carried out by said device a robust detection of each respiratory cycle of the respirating person is accomplished. In an advantageous manner the transition from the inspiratory phase into the expiratory phase happens via a characteristic flank on the basis of which a secure detection of each breathing cycle is enabled. In a preferred manner the first derivation in time is estimated. The local extremes of the estimated first derivation of the flow-function correspond to the maximum inclination of the respiratory flow during transition between inspiration and expiration. Beginning in the expiration phase the starting point of Inspiration is detected in that a search through the preceding extreme of the estimated second derivation is carried out. Further preferred embodiments of the invention are subject of the dependent claims.

The length of the first time period is preferably set so as to extend over at least two breathing cycles. Preferably a second means is provided for provision of a second signal indicative with respect to the dynamic and/or static pressure of the respiratory gas. In a preferred manner there is provided at least one filter means for filtering or damping the first and/or second signals.

The signal processing means preferably includes a smoothing means, for smoothing the reference relation by use of selected smoothing criteria. Said smoothing criteria are preferably adaptively changed. The signal processing means preferably includes a smoothing means for smoothing or damping said reference relation.

At least one of said smoothing means is preferably construed so as to effect smoothing on the basis of statistical solution-statements. The signal processing means preferably includes a threshold consideration means for evaluating said correlation-relation with respect to threshold criteria in particular zero crossing. The signal processing means preferably includes a counting means for counting performance of predetermined criteria within a preset period of time. The filter- and/or smoothing parameters are preferably adaptively fitted.

The object of the present invention as mentioned at the beginning is further solved by a device for supplying respiratory gas to a patient at excess-pressure via a feeding means for feeding said respiratory gas and a detection means for detecting at least the breathing gas pressure and/or the breathing gas flow, characterized by a signal processing means generating a reference relation on the basis of the detected signals and which is setting the breathing gas pressure on the basis of a correlation between said reference relation and the present breathing patterns.

The object mentioned at the beginning is further also solved by a method for controlling the respiratory gas pressure during CPAP-therapy, by detecting signals indicative with respect to the breathing gas pressure and the breathing gas flow, wherein on the basis of the time related dynamic of the measuring values of pressure and respiratory gas flow the presence and/or degree of a flow limitation is detected and the breathing gas pressure is controlled accordingly.

In one embodiment, the time-points of the beginning of Inspiration- and/or Expiration are determined in consideration of the inclination of a curvature portion of the gas flow by using statistic smoothing methods and wherein a significant variation of the distance between the ends of Inspiration- or Expiration is determined with respect to a number of subsequent breathing cycles.

In a advantageous manner irregularities within the breathing gas flow are detected by comparing the present breath with timely preceding breathings by application of statistical dependency measurements Preferably correlation-coefficients and/or mutual-informations are detected as measurements of dependency.

Preferably a correlation relation between a reference function and a present breathing flow is generated, wherein in case of to little statistical dependency between the present breath and the timely preceding breath the respiratory pressure is adjusted accordingly.

Preferably groups of breathings are standardized via affine transformation wherein the average curvature of the standardized breath is used for detection of probably existing flow limitations.

Further the object mentioned at the beginning is also solved by a method for controlling the breathing gas supply pressure during CPAP-therapy by detection of the sleeping position of the patient, in particular the head-position, and/or torsi-position or neck-torsion-degree and wherein the respiratory target pressure and/or the pressure control characteristic of the breathing gas supply is set in dependency of those detections.

According to a further aspect of the present invention the object mentioned at the beginning is solved by a method for controlling the breathing gas supply during CPAP-therapy including detection of a signal indicative with respect to breathing gas flow, and subjecting this signal a correlation-analysis on the basis of an adaptively actualized reference function, wherein on the basis of the results of the correlation analysis the physiological state of the patient is typified, wherein with respect to the control of the respiratory gas pressure, in particular with respect to setting a respiratory target pressure, the control characteristic of a respiratory gas pressure control means is adapted.

Preferably there are provided several pressure control modes adapted for selected sleep-stages of the patient. The sleeping position of the patient, in particular the head- and/or torsi-position, and/or the neck torsion degree are preferably detected in association herewith and the breathing gas target pressure and/or the pressure control characteristic of supplying respiratory gas is set in consideration of these detections also.

Further the object mentioned at the beginning is also performed by a method for controlling the supply of respiratory gas pressure during CPAP-therapy, including detection of a first signal indicative with respect to breathing gas flow, wherein this signal subjected to a correlation analysis based on an adaptively actualized reference function, wherein on the basis of the results of said correlation analysis a physiological state of the patient is typified, wherein in dependency of the result of typification the breathing gas pressure control is adjusted in such a manner, that same adjusts substantially equal static respiratory gas pressure values for inspiration and expiration within a mask region,—or different mask pressure values for inspiration and expiration (bilevel-mode).

Further details and features will be apparent from the following description with reference to the drawings in which:

FIG. 1 shows (top) a data-portion of a flow graph of a patient during NREM2;
  (middle) a high vertical line indicating the end of inspiration, a low line indicating the start of inspiration;
  (bottom) the first derivation in time of the flow-graph on the basis of which the end and the beginning of inspiration may be detected FIG. 2 shows (top) a data portion of a flow graph of a patient during NREM 2;
  (middle) the last breathing cycle of the data sequence above selected as reference relation for the breathing pattern;
  (bottom) correlation between the data portion above (reference relation) and the flow pattern in the midst;

Figure 1:
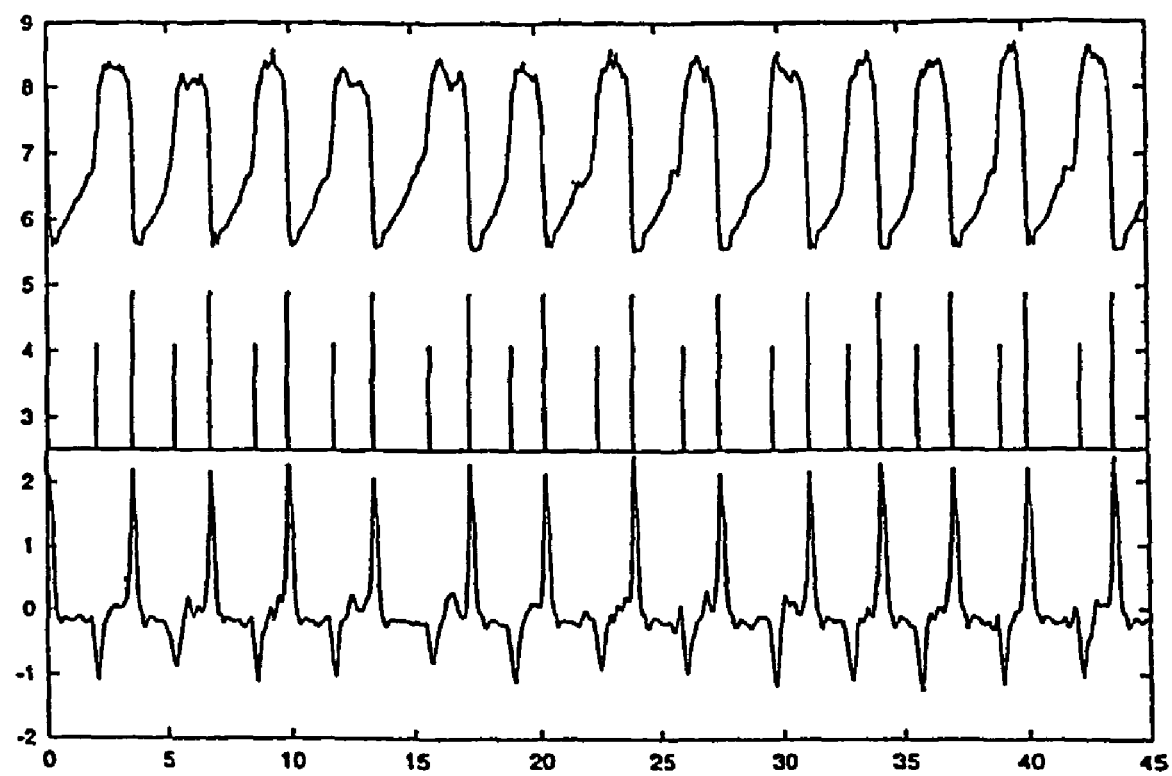

In FIG. 1 the top graph displays 45 seconds of a flow graph of a patient at NREM2-sleep stage. The lower graph of this figure shows an estimated first derivation of the flow graph. Between both graphs the hereby automatically detected transition points are indicated by vertical lines.

Figure 5:
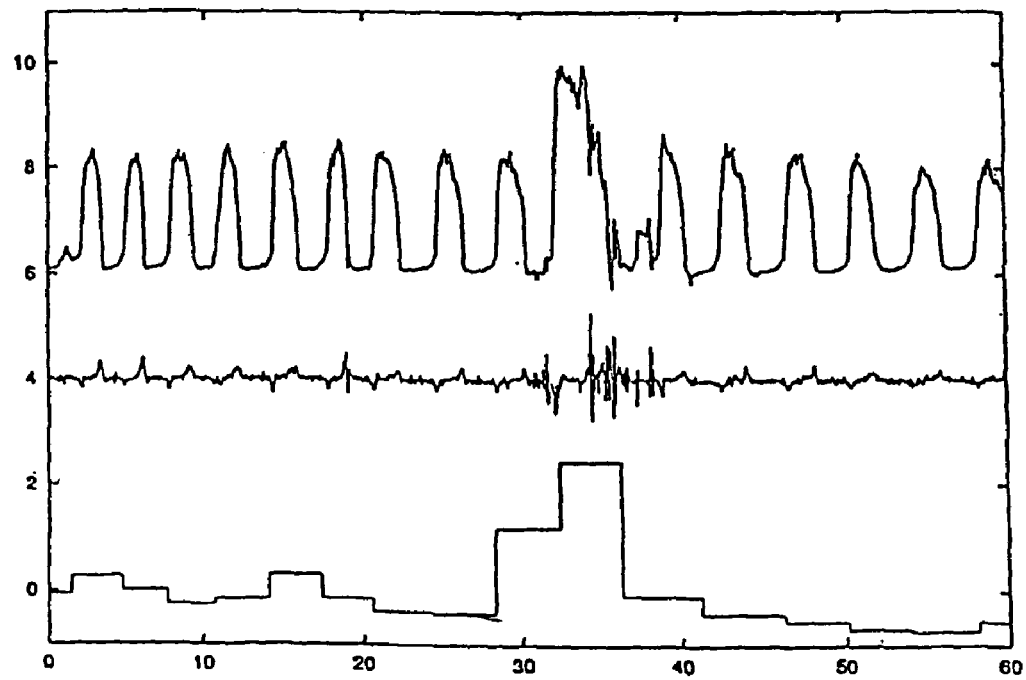
FIG. 5 shows (top) a data portion of the flow graph of a patient;
  (middle) associated CPAP-pressure graph;
  (bottom) variance of the CPAP signal per breathing cycle.
Figure 6:
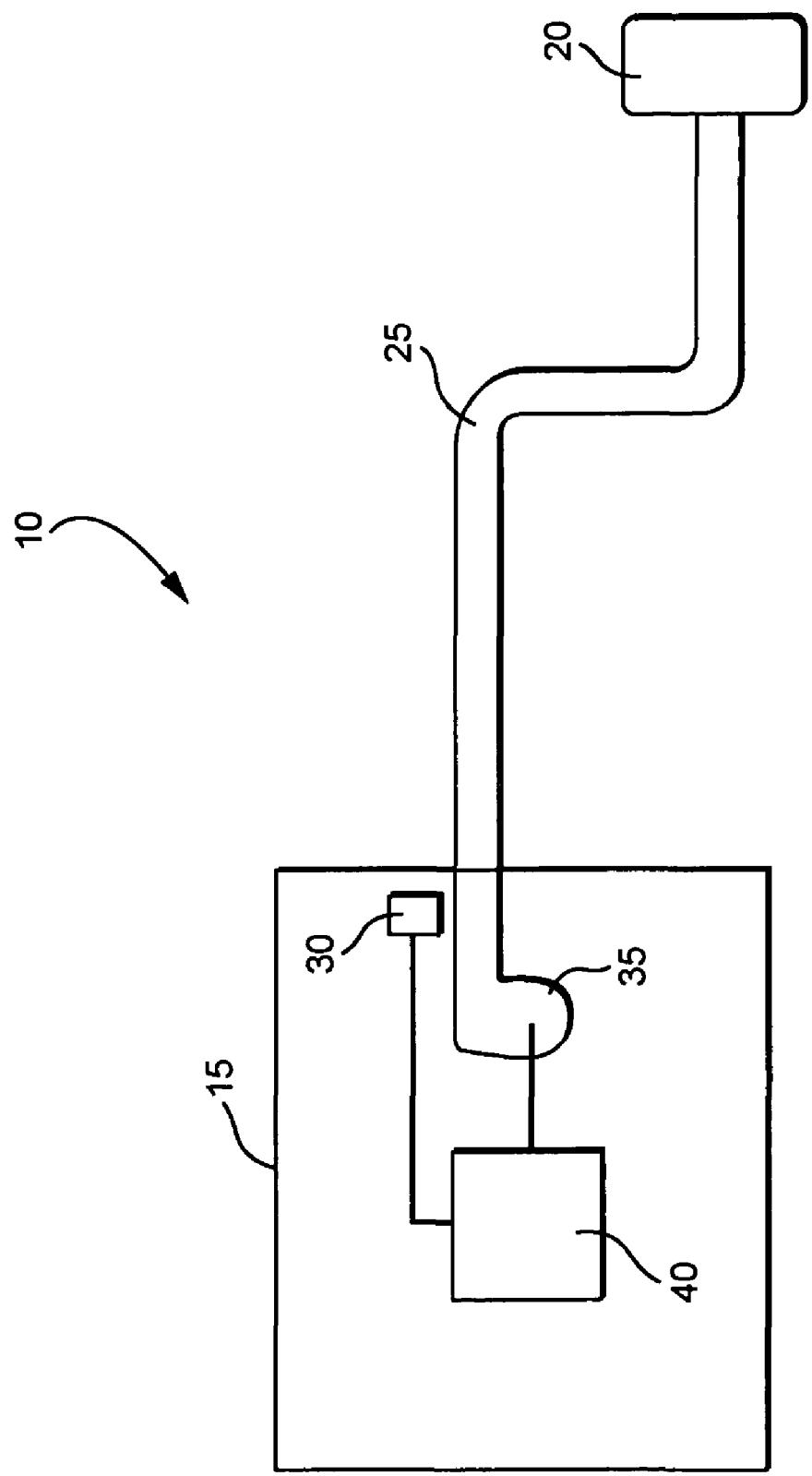
FIG. 6 is a schematic view of a device according to an embodiment of the present invention.

FIG. 6 is a schematic view of a device 10 constructed according to an embodiment of the present invention. Device 10 can be used to carry out the processing described below in relation to FIGS. 1-5. Device 10 includes a flow generator 15, a patient interface 20, e.g., a breathing mask, and a breathing gas conduit 25 to deliver pressurized gas from the flow generator 15 to the patient interface 20. Flow generator 15 typically includes a detector 30 to produce a signal relating to breathing gas pressure (e.g., via a pressure sensor) and/or breathing gas flow (e.g., via a flow sensor or meter). Flow generator 15 includes a processor 40, e.g., in the form of a CPU, to receive input signals from the detector 30. Processor 40 is adapted to generate a reference-relation on the basis of the detector signal to adjust the breathing gas pressure on the basis of a correlation-relation between the reference-relation and a prevailing breathing pattern of the patient.

For differentiation between stable and non-stable respiration, a measurement of similarity of a plurality of successive breathing cycles is considered. The height of a cross-correlation-function is an appropriate measurement for the similarity of the present breathing cycle with preceding breathing cycles. The top graph shown in FIG. 1 thereby illustrates the breathing gas flow of a patient during NREM2 sleep stage. The high vertical line of the middle graph indicates the end of inspiration, the lower vertical line of the middle graph indicates the end of expiration. The first derivation of the flow graph which allows detection of the end and the beginning of inspiration is illustrated as the lower graph. Because of the different extrema of the first derivation of the flow graph it is possible to reliably distinguish between individual breathing phases.

Figure 2:
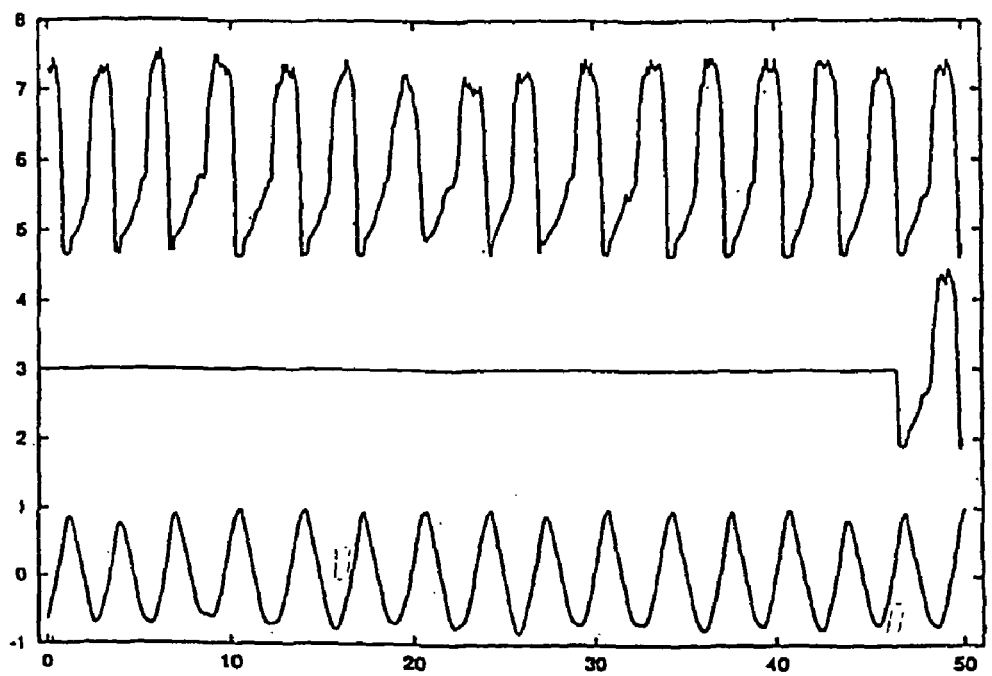

The FIG. 2 graph illustrates as an example a 50-second portion of respiratory flow of a patient during NREM 2. The middle graph is a selected breathing cycle (e.g., a non-averaged reference-relation equivalent to a measured prior flow of breathing gas of the person from at least one breathing cycle of the person). The lower graph illustrates the correlation between the data sequence (top graph) and said selected breathing cycle. The correlation graph assumes values between 1 and −1, wherein the correlation assumes the value 1 in case that both breathing cycles correspond to each other exactly,—and the correlation assumes the value −1 when the graphs are correlated negative i.e. a top section of breathing pattern exactly meets a valley section of the analyzed data portion.

On the basis of the correlation graph it is at first evident whether respiration is regular and at second whether breaths are missed completely. In case where successive breathing cycles are similar the graph of correlation will have a periodic course with local maxima close to 1 and local minima close to −1.

With respect to the correlation graph illustrated in FIG. 2 the difference to the value 1 is calculated at each local maxima, wherein all of the thus obtained values are averaged. This average value between 0 and 1 may be used as a measurement in how far the breathing pattern corresponds to the preceding breathing cycles.

Figure 3:
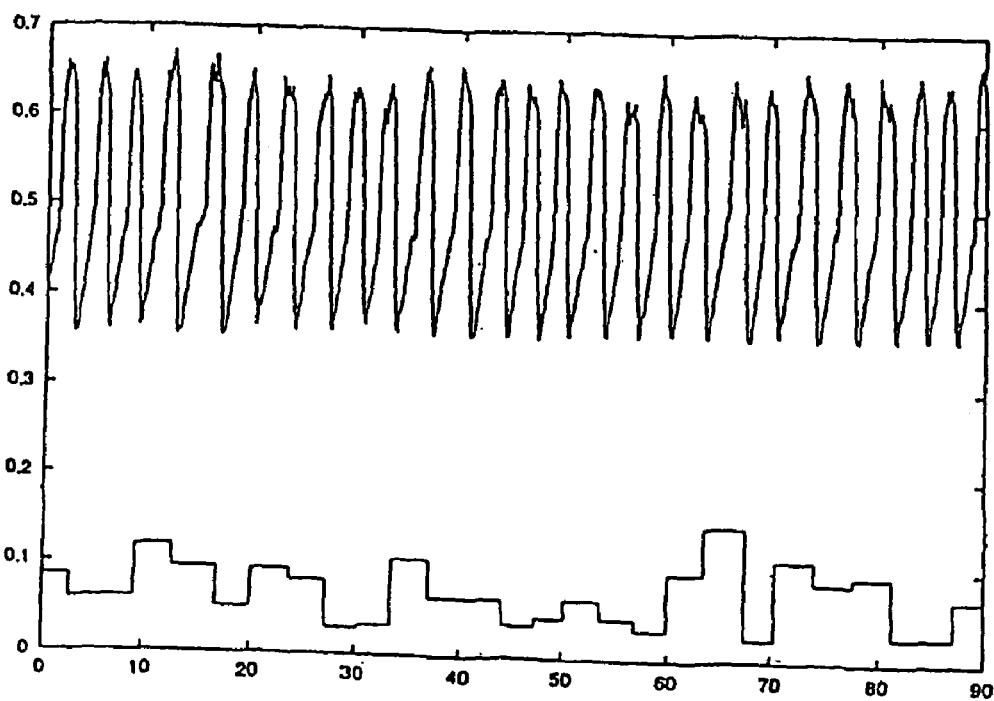
FIG. 3 shows (top) a data portion of a flow graph of a patient during NREM2;
  (bottom) the average difference of the maxima of correlation from the value 1.

In FIG. 3 the top graph illustrates the flow graph of a patient during NREM 2 sleep stage. The lower data sequence illustrates the average difference of the maxima of correlation to the value 1.

Figure 4:
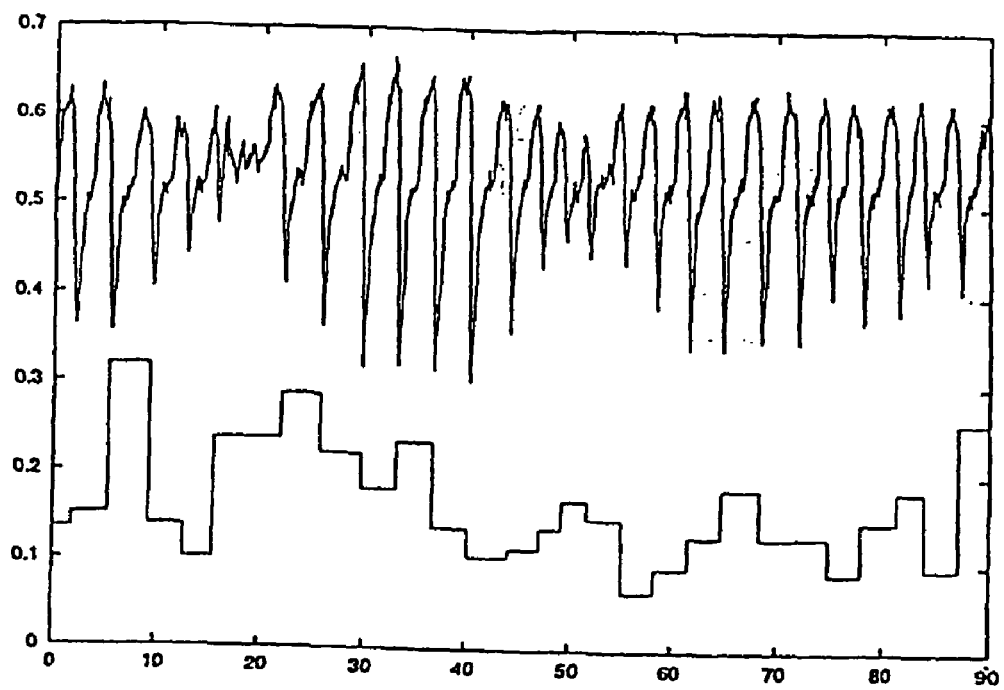
FIG. 4 shows (top) a data portion of the flow graph of a patient during REM;
  (bottom) average difference of the maxima of correlation from the value 1.

FIG. 4 basically corresponds to FIG. 3 however the flow graph here results from REM-sleep stage. The comparison of the average maxima of correlation according to FIGS. 3 and 4 shows that the average difference of the maxima of correlation to 1 in REM sleep stage is clearly greater.

The following table illustrates which groups of respiratory states could be differentiated on the basis of the measurement of similarity as set forth above.

| stable respiration | non stable respiration |
| --- | --- |
| silent regular respiration | irregular respiration during REM |
| respiration with associated snoring | obstructive apnea |
| mouth breathing | awake respiration |
| Periodic breathing with flow limitation | Cheyne Stoke respiration |
| dampened respiratory flow signal | |

Detection of Snoring

The detection of snoring may be effected according to a preferred embodiment of the invention on the basis of the variance of the CPAP-pressure within a breathing cycle. In FIG. 5 the top graph illustrates a portion of a respiratory flow signal, there under there is illustrated the corresponding CPAP-pressure. The graph bottom illustrates the variance of the CPAP-pressure per breath. Said variance clearly increases when the CPAP-Signal is varied due to patients snoring.

Further Parameters of Discernment

The reliable detection of the transition points for beginning and end of inspiration on the basis of the concept according to the present invention allows to retrieve further significant features for distinguishing of breathing states. Particular advantageously retrievable indications are the time of inspiration, the time of expiration, the maximum flow during inspiration, the maximum flow during expiration, the volume of inspiration and the volume of expiration.

Mouth Breathing artefacts due to mouth-breathing may be reliably detected since in that case a negative correlation is existing. Obstructive apneas might be detected also in that certain peaks of correlation occur in a clearly weakened manner—or are completely missing in the regular case.

Flow Limited Breathing

On the basis of the concept underlying the present invention a flow limited breathing may be made out via the volume of inspiration or the relative change of the maximum inspiratory flow, in as far as inspiration is flow limited. If the approximate moments for beginning and end of inspiration are known it is possible to determine the moment of maximum inspiration. If this moment is placed in the first half of inspiration the presence of a flow limited inspiration may be assumed with high statistical likelihood and a respective correction of the respiratory pressure may be administered.

Cheyne Stoke Respiration

A periodic course of respiration showing periodic course of the inspiratory volume is characterizing Cheyne Stoke respiration which is thus distinguishable from other non stable breathing patterns.

Surveillance of the Detected Breaths

In a quite advantageously manner the correlation curve may be used for surveillance of the detected moments of beginning and end of inspiration, since a local maxima in the correlation graph is representing with high statistical safety a feature of a breath.

On the basis of the concept of analysis underlying the device according to the present invention it is possible to detect individual breath with high statistical likelihood and to make far reaching conclusions with respect to the present condition of the patient. Via the thus obtained detections it will become possible to adjust the therapy pressure in a predictive manner and with comparatively small changing-gradients in line with the physiological needs of the patient. This affords to a high acceptance of therapy.

The invention claimed is:

1. A method for detecting the breathing activity of a person, the method comprising:
generating a first signal related to a flow of breathing gas provided to the person by a PAP device;
generating a non-averaged reference-relation equivalent to a measured prior flow of breathing gas of the person from at least one breathing cycle of the person;
comparing the reference-relation to the first signal;
generating a correlation-relation based at least in part on the comparison between the reference-relation and the first signal; and
generating an output signal related to the person's breathing activity and/or physiological condition based at least in part on the correlation-relation.

2. The method of claim 1, further comprising adjusting pressure of the breathing gas in response to the output signal.

3. The method of claim 1, wherein the prior flow corresponds to at least two breathing cycles.

4. The method of claim 3, wherein the comparing compares the first signal to each measured prior flow.

5. The method of claim 1, further comprising generating a second signal related to pressure of the breathing gas.

6. The method of claim 5, further comprising filtering and/or dampening the first signal and/or the second signal.

7. The method of claim 6, wherein the first signal and/or the second signal are filtered and/or dampened based on at least one adaptively changed parameter.

8. The method of claim 1, further comprising smoothing the reference-relation.

9. The method of claim 8, wherein the reference-relation is smoothed based on at least one adaptively changed smoothing criterion and/or at least one statistical concept.

10. The method of claim 1, wherein the correlation-relation is further based on threshold criteria.

11. The method of claim 10, wherein the threshold criteria is zero-crossings.

12. The method of claim 1, further comprising counting each occurrence of one or more criteria.

13. The method of claim 1, wherein the generating of the reference-relation comprises assessing the prior flow of breathing gas over one or more entire breathing cycle(s).

14. The method of claim 13, further comprising determining whether any patterns in local maxima and minima in the correlation-relation exist across multiple breaths.

15. A method of treating a patient for sleep-disordered breathing, the method comprising:
providing a supply of pressurized breathable gas to the patient from a PAP device;
generating a signal related to flow and/or pressure of the supply of pressurized breathable gas;
generating a non-averaged reference-relation equivalent to a previous supply of pressurized breathable gas during a time period;
comparing the reference-relation to the signal;
determining a correlation-relation based at least in part on the comparison of the reference-relation and the signal;
generating an output signal related to the person's breathing activity and/or physiological condition, the output signal being based at least in part on the correlation-relation; and
adjusting the flow and/or pressure of the pressurized breathable gas provided by the PAP device in response to the output signal.

16. The method of claim 15, wherein the time period is at least two breathing cycles.

17. The method of claim 15, wherein the generating of the reference-relation comprises assessing the previous supply of pressurized breathable gas over one or more entire breathing cycle(s).

18. A method of monitoring breathing gas supplied to a patient above ambient pressure, the method comprising:
generating a signal related to breathing gas pressure and/or breathing gas flow of a current breathing pattern of the patient;
generating a non-averaged reference-relation signal equivalent to breathing gas pressure and/or breathing gas flow on a previous breathing pattern of the patient;
comparing the reference-relation signal to the signal so as to derive a correlation-relation therefrom; and
adjusting the breathing gas pressure and/or flow provided from a PAP device based at least in part on the correlation-relation between the reference-relation and the signal.

19. A PAP device, comprising:
a controllable flow generator operable to generate a breathing gas flow for a patient;

a sensor operable to generate at least one signal directly related to a gas flow and/or pressure supplied to the patient; and a processor operable to generate:
  a non-averaged reference-relation based at least in part on a portion of the signal, the portion equivalent to a previous breathing gas flow for the patient,
  a correlation-relation derived from a comparison between the reference-relation and the at least one signal, and
  an output signal related to the patient's breathing activity and/or the patient's physiological condition based at least in part on the correlation-relation.

20. The PAP device of claim 19, wherein the processor is further operable to cause the flow generator to alter the breathing gas flow and/or pressure in response to the output signal.

21. The PAP device of claim 19, further comprising a filter, operable to filter and/or dampen a frequency range from the at least one signal.

22. The PAP device of claim 21, wherein the frequency range corresponds to the patient's snore.

23. The PAP device of claim 19, wherein the processor is further operable to smooth the reference-relation.

24. The PAP device of claim 19, wherein the portion constitutes one or more entire breathing cycle(s).

* * * * *